United States Patent [19]

Jacoby et al.

[11] 4,191,054
[45] Mar. 4, 1980

[54] ATMOSPHERIC SAMPLING APPARATUS

[75] Inventors: Marvin Jacoby, Rochester, N.Y.;
Richard Jacoby, Haverford, Pa.;
Robert Ellson, Rochester, N.Y.

[73] Assignee: Air Test Labs, Inc., Rochester, N.Y.

[21] Appl. No.: 953,349

[22] Filed: Oct. 23, 1978

[51] Int. Cl.$^2$ ............................................. G01N 1/24
[52] U.S. Cl. ............................................. 73/421.5 R
[58] Field of Search ................................... 73/421.5 R

[56] References Cited

U.S. PATENT DOCUMENTS

| | | | |
|---|---|---|---|
| 1,128,669 | 2/1915 | Ellison | 73/421.5 R |
| 3,618,393 | 11/1971 | Principe et al. | 73/421.5 R |

FOREIGN PATENT DOCUMENTS

| | | | |
|---|---|---|---|
| 632179 | 11/1949 | United Kingdom | 73/421.5 |
| 756186 | 8/1956 | United Kingdom | 73/421.5 R |

*Primary Examiner*—S. Clement Swisher
*Attorney, Agent, or Firm*—Robert S. Beiser

[57] ABSTRACT

An improved apparatus for collecting atmospheric samples, particularly air samples, comprises a sealed first container filled with liquid such as water, a sealed second container positioned below the first container, a vent in the first container which allows the atmosphere surrounding the apparatus to enter the first container at a controlled rate, and a vent from the second container for dispersing the atmosphere contained within the second container into the surrounding atmosphere at a controlled rate. A flow channel between the first and second containers allows the liquid in the first container to pass into the second container. Passage of the liquid from the first container to the second container creates a vacuum in the first container whereby a stream of air from the surrounding atmosphere is drawn at a controlled rate through the first container vent and into the first container where it is retained. Samples may be withdrawn from the first container through the use of a hypodermic syringe.

15 Claims, 1 Drawing Figure

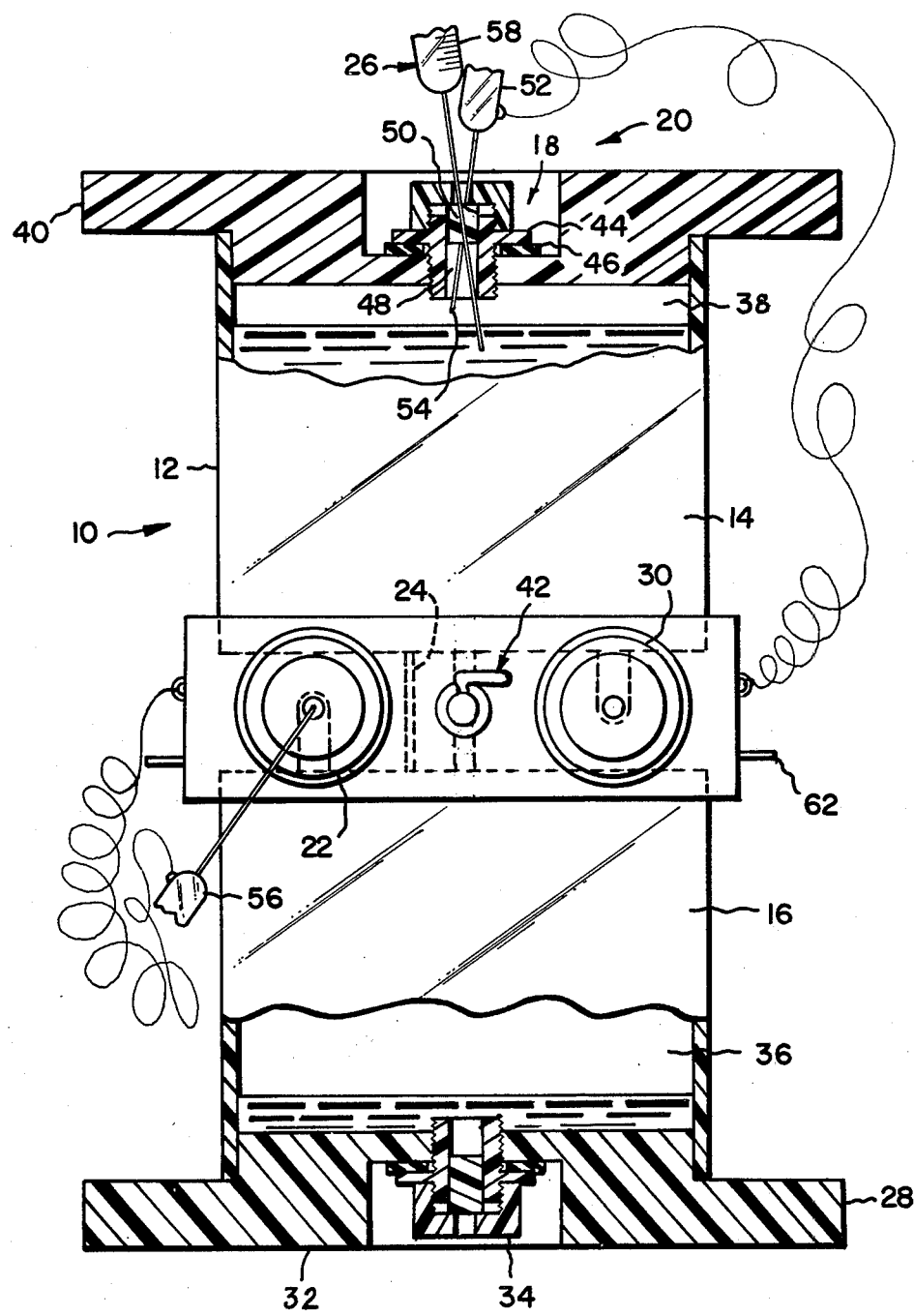

ATMOSPHERIC SAMPLING APPARATUS

BACKGROUND OF THE INVENTION

The present invention relates generally to devices for obtaining gaseous samples in general and for obtaining air samples in particular.

In recent years the attention of the public has increasingly focused on the dangers of air pollution. Along these lines the United States government has established clean air standards which are administered by the Environmental Protection Agency and the Occupational Safety and Health Administration. In order to determine the presence and extent of harmful chemicals and particulate matter in the air, systematic and scientific sampling must be conducted.

One particular area of concern in recent years has been exposure by hospital operating room personnel to commonly used gaseous anaesthetics. In order to prevent exposure to excessive levels of such anaesthetics, several devices have been developed for sampling the atmosphere in hospital operating rooms so that the samples can be chemically analyzed in order to determine the extent of such anaesthetic contamination. Among such devices are those of Calibrated Instruments Incorporated and Boehringer Laboratories which utilize a vacuum pump to inject a quantity of the air within the operating room into a sample receptacle for later chemical analysis.

However, several problems have remained in obtaining samples of operating room air. Primary among these is the fact that an electric pump is required to collect the air samples. The danger of explosion being extremely high in operating rooms due to the flammable nature of the anaesthetic gases, such electrical devices must be shock proof, making them extremely expensive. In addition, such vacuum pumps tend to be expensive to operate either in the use of electricity or in batteries.

An additional problem in this regard is that devices presently available utilize flexible bags for obtaining samples. These bags are relatively high in cost and tend to leak over a period of time, necessitating replacement.

Therefore, it is an object of the present invention to provide an apparatus for obtaining air samples in operating rooms which does not require the use of electric motors; and to provide such an air sampling apparatus utilizing air collection containers which are reuseable and remain airtight over an extended period of time.

SUMMARY OF THE INVENTION

The present invention is an improved apparatus for collecting atmospheric samples, particularly air samples. The apparatus comprises a first sealed container or chamber filled with a selected quantity of liquid, (in a preferred embodiment the container holds 1.25 quarts) and a second sealed container (also holding 1.25 quarts in a preferred embodiment). The first container has a venting mechanism which controlledly introduces the atmosphere surrounding the apparatus into the first container. By controlledly introducing it is meant that the atmosphere may be selectively drawn into the container when desired at a controlled rate, and that the atmosphere within the container does not exit through the venting mechanism. The venting mechanism for the second container controlledly disperses the atmosphere within the second container out into the surrounding atmosphere. A flow channel between the first and second containers allows the liquid contained in the first container to pass into the second container at a controlled rate. The rate is controlled by the size of the channel and the volume of the containers. The passage of the liquid through the channel creates a vacuum in the first container thereby drawing a stream of the surrounding atmosphere through the first container vent and into the first container where it is retained. A sample removal system is provided which permits withdrawal of a desired quantity of the retained atmosphere from the first container. In a preferred embodiment, the sample removal system consists of a hypodermic syringe which is inserted through the venting mechanism for withdrawal of the sample. A base is also provided for supporting the entire apparatus.

In a preferred embodiment of the apparatus either the first container or the second container may be used for collecting samples. In the first operating mode of the invention the second container is positioned below the first container. The previously mentioned liquid material initially fills the first container. A vent is positioned at the top of the first container for allowing controlled introduction of the atmosphere surrounding the apparatus into the first container. A vent is located in the center of the apparatus and connected to the second container which allows dispersal of atmosphere within the second container out into the surrounding atmosphere. Again, a flow channel runs between the first and second containers which allows the passage of liquid therethrough. In the first operating mode, the passage of liquid is from the first container to the second container, thereby creating a vacuum in the first container and thus drawing a continuous stream of the surrounding atmosphere through the top vent of the first container and into the first container.

In the second operating mode the second container is positioned above the first container. The previously mentioned liquid initially fills the second container. A vent located in the center of the apparatus connected to the first container allows air within the first container to be dispersed out into the atmosphere. A vent is located at the top of the second container, (bottom when inverted), which allows introduction of the atmosphere surrounding the apparatus into the second container. Again, a flow channel runs between the first and second containers which allows the passage of liquid therethrough. The passage of liquid is from the second container to the first container, thereby creating a vacuum in the second container, thus drawing a continuous stream of the surrounding atmosphere through the top vent of the second container and into the second container. A sample may be removed from either container by inserting a hypodermic syringe into the top vent of the container being filled with the surrounding atmosphere. A base is formed at both the top and bottom of the apparatus so that the device may be inverted in order to permit operation in the first or second mode.

An additional feature of the invention is a quick drain valve positioned between the first and second containers which allow rapid drainage of the liquid from one container into the other so that if rapid completion of a cycle is desired, it may be accomplished by draining the liquid thereby preparing for a new cycle.

In a preferred embodiment the venting mechanism utilized in the apparatus both at the top of the apparatus and in the central portion comprises a septum holding member which is attached to the container which it vents; i.e. allows atmosphere to pass into or out of the container. The septum holding member forms an airtight seal with the container. In a preferred embodiment this is accomplished by threadedly attaching the septum holding member to the container and having a gasket therebetween. Through the septum holding member is a passageway which, in a preferred embodiment, is circular. A septum or solid disc of material, in a preferred embodiment being silicone rubber, is securely positioned within this passageway and forms an airtight seal with the passageway through a pressed fit therein. A hollow needle member, in a preferred embodiment being a hypodermic needle, is insertable through the septum whereby a gaseous atmosphere may pass into or out of the container.

One of the features of the invention is the fact that it is reversible; either the first or second container may be utilized to obtain atmospheric samples. In the first operating mode of the preferred embodiment of the invention, a hollow needle, preferably a hypodermic needle, is positioned through the vent at the top of the first container. A hollow needle is also positioned through the central vent connected to the second container whereby the atmosphere surrounding the apparatus is permitted into the first container and the atmosphere within the second container is permitted to be dispensed therefrom. This allows the liquid in the first container to pass into the second container below it, due to atmospheric pressure acting upon the liquid in the first container and the liquid passing into the second container displacing the atmosphere contained within the second container. In a second operating mode of the preferred embodiment of the invention, the first and second containers are inverted. A hollow needle is positioned through the vent at the top of the second container and a hollow needle is positioned through the central vent leading to the first container so that the atmosphere surrounding the apparatus is introduced into the second container displacing the liquid therein, thereby permitting the liquid to pass from the second container into the first container. This liquid displaces the atmosphere already within the first container, which is dispensed out of the central vent for the first container.

One of the key aspects of the invention is the restrictive flow channel which connects the first and second containers. The channel comprises a tubular member having an orifice therethrough or in a preferred embodiment merely the orifice itself. The orifice, in a preferred embodiment, has a diameter of 0.0032 inches whereby the liquid may pass from one container to another. However, the size of the orifice restricts the flow of the liquid sufficiently so that a desired period of time, (in a preferred embodiment, 4 hours), occurs during which the atmospheric samples are drawn. The period of time during which sampling occurs can be modified by increasing or decreasing the size of the orifice as well as increasing or decreasing the size of the containers. Additionally, the time period can be modified by selection of a liquid medium which has a higher viscosity than water, thereby slowing the rate of flow.

In order to obtain samples from the apparatus, a hypodermic syringe is inserted through the septum of the venting mechanism and into the container to be sampled. A quantity of the atmosphere within the container is drawn out through the syringe. This syringe is then injected into a sealed vacuum tube which retains the sample therein. In a preferred embodiment the syringe has a capacity of 25 CC and the sample injected into the vacuum tube has a volume of approximately 18 CC.

One of the advantages of the apparatus is that it provides a method of obtaining samples using a Time Weighted Average system. By this it is meant that atmosphere is drawn into the container continuously over a selected period of time such as a 4 hour period. A sample is then drawn from the container and the sample is analyzed. The chemical constituents present in the sample represent the average presence of such chemicals or particulate matter over a 4 hour period, rather than showing the greatest concentration or the least concentration in any particular time during that 4 hour period.

An additional feature of the invention is a number of needle holding members affixed to the apparatus which are designed to retain the hypodermic needle utilized in venting the first and second containers. In a preferred embodiment there are two needle holding members which hold the two needles necessary to vent the first and second containers so as to operate the apparatus. In a preferred embodiment the desired size of needle is a Size 20 hospital hypodermic syringe.

The apparatus may be constructed of a wide variety of material such as metal, glass or plastic, so long as it is properly sealed. However, in a preferred embodiment the apparatus is constructed of clear acrylic plastic which is light in weight, inexpensive and permits viewing of the level of liquid in the containers.

BRIEF DESCRIPTION OF THE DRAWING

The drawing is a front view, partially in cross section, of an improved atmospheric sampling apparatus.

DETAILED DESCRIPTION OF THE PREFERRED EMBODIMENT

While this invention is susceptible of embodiment in many different forms, there is shown in the drawing and will herein be described in detail, several specific embodiments, with the understanding that the present disclosure is to be considered as an exemplification of the principles of the invention and is not intended to limit the invention to the embodiments illustrated.

Improved atmospheric sample collection apparatus 10, as shown in the drawing, comprises a sealed first container member 12 filled with a liquid material 14. A sealed second container 16 is positioned below the first container 12. A venting mechanism 18 is positioned at the top of first container 12 which when activated introduces the gaseous atmosphere 20 surrounding apparatus 10 into first container 12. A second container venting mechanism 22 which is highly similar to the first container venting mechanism 18 is positioned proximate to the center of apparatus 10 so as to be above second container 16. This second container venting mechanism 22, when activated, disperses the atmosphere within the second container 16 into the surrounding atmosphere 20. A flow channel 24 between the first container 12 and the second container 16 allows the passage of liquid 14 from the first container into the second container. The rate of passage of liquid 14 is controlled by the size of flow channel 24 as well as the quantity of liquid 14 contained in first container 12. The passage of liquid 14 from the first container 12 to the second container 16 creates a vacuum in first container 12 whereby a portion of surrounding atmosphere 20 is controlledly drawn through the first venting mechanism 18 and into the first container 12 where it is retained. Sample removal means 26, in the preferred embodiment being a hypodermic syringe which is insertable through first container venting means 18 permits withdrawal of a desired quantity of atmosphere 22 which has been retained within the first container 12. A base 28 is also provided for supporting the apparatus.

In a preferred embodiment apparatus 10 in the first operating mode has second container member 16 positioned below first container member 12. In the second operating mode of the invention the containers are inverted; second container 16 is positioned above first container 12. Liquid material 14 in the first operating mode initially fills first container 12. In the second operating mode liquid material 14 initially fills second container 16. At the top of first container 12 is a venting mechanism 18 which is used to allow introduction of the atmosphere 20 surrounding the apparatus into first container 12 in the first operating mode. At the center of the apparatus is an additional venting mechanism 30, in the claims called first container central venting means, which is used in the second operating mode, where the apparatus 10 is inverted, for venting the atmosphere in first container 12 into the atmosphere surrounding the apparatus 10. At the top 32 of second container 16 is an additional venting mechanism 34, in the claims called second container top venting means, which is used for the controlled introduction of atmosphere 20 surrounding apparatus 10 into second container 16 in the second operating mode of the invention. It should be noted that what is called the top 32 of second container 16 as positioned at the bottom of the apparatus 10 in the first operating mode and at the top of the apparatus 10 in the second operating mode. An additional venting mechanism 22 is positioned at the center of apparatus 10 for controlled dispersal of the atmosphere 36 in second container 16 out of the apparatus 10 and into the atmosphere outside. Flow channel 24 between first container 12 and second container 16 allows liquid 14 to pass therethrough. In the first operating mode the passage of liquid 14 from container 12 to container 16 creates a vacuum in container 12. In a second operating mode liquid 14 passes from container 16 to container 12 creating a vacuum in container 16. In the first mode the vacuum draws a continuous stream of surrounding atmosphere 20 through first container top vent mechanism 18 and into container 12. In the second operating mode a continuous stream of surrounding atmosphere 20 is drawn through second container top venting mechanism 34 and into second container 16. Sample removal means 26 permits withdrawal of a desired quantity of retained atmosphere such as atmosphere 38 retained within first container 12. Upper base 40 provides for the support of apparatus 10 in the second operating mode of the invention.

An additional feature of the invention is the quick drain valve 42 positioned between first container 12 and second container 16 whereby liquid 14 may be quickly drained from first container 12 into second container 16, or vice versa, thereby quickly and easily preparing apparatus 10 for a new sampling cycle.

First container top venting mechanism 18, second container central venting mechanism 22, first container central venting mechanism 30 and second container top venting mechanism 34 are all constructed, in a preferred embodiment, identically. For purposes of illustration the venting mechanism described will be first container top venting mechanism 18. The venting mechanism 18 comprises a septum holding member 44 attached to first container 12 and extending therein. Septum holding member 44 forms an airtight seal with container 12 by means of gasket 46. Septum holding member 44 has a passageway 48 through its center and running along its length which extends into container 12. A septum 50 positioned within passageway 48 forms an airtight seal within passageway 48. A hollow needle member 52, such as those commonly used in hospital syringes having an aperture 54 near its tip is insertable through septum 50 so that gaseous atmosphere 20 may pass into first container 12.

In a preferred embodiment either first container 12 or second container 16 may be utilized to obtain atmospheric samples. In the first operating mode hollow needle member 52 is positioned in first container top venting means 18 and hollow needle member 56 is positioned through second container central venting mechanism 22. As a result, the atmosphere 20 surrounding apparatus 10 is permitted to be introduced into first container 12 and atmosphere 36 within second container 16 is permitted to be dispensed from container 16. This permits liquid 14 to pass from first container 12 into second container 16 below it.

In the second operating mode of the invention first container 12 and second container 16 are inverted. Hollow needle 56 is positioned through second container top venting means 34. Hollow needle member 52 is positioned through first container central venting mechanism 30. As a result, the atmosphere 20 surrounding apparatus 10 is permitted to be introduced into second container 16 and the atmosphere 38 within first container 12 is permitted to be dispersed therefrom through venting mechanism 30. As a result, liquid 14 passes from second container 16 into first container 12 below it which creates a vacuum in second container 16 so as to draw surrounding atmosphere 20 therein.

In a preferred embodiment restrictive flow channel 24 has a diameter of 0.0032 inches so that the passage of liquid 14 therethrough is restricted, but permitted.

In a preferred embodiment sample removal means 26 comprises a hypodermic syringe 58 used for withdrawal of a desired quantity of the atmosphere to be sampled from the apparatus 10 through insertion into the container to be sampled which as illustrated is container 12. In order to safely and easily transport the sample for later chemical analysis, a sealed vacuum tube (not shown) commonly used in hospitals and for chemical testing is injected with the atmospheric sample in syringe 58. The vacuum tube may then be transported for later testing.

Because atmosphere 20 is continuously drawn into apparatus 10 over an extended period of time it is possible to obtain samples which have a Time Weighted Average concentration of contaminants. This is due to the small size of aperture 54 in hypodermic needle 52, and the small size of flow channel 24. As a result, liquid 14 flows from first container 12 to second container 16 or vice versa over an extended period of time, thereby allowing a Time Weighted Sample. In addition, the use of electric motors is not required.

A further feature of the invention are needle holders 60 and 62 affixed to apparatus 10 for retention of hollow needle members 52 and 56. These are provided for the convenience of the user. In a preferred embodiment hollow needle members 52 and 56 contain a Size 20 hypodermic needle. As a result, in a preferred embodiment, the surrounding atmosphere is drawn into apparatus 10 over a period of 4 hours.

Although the apparatus could be constructed of many different materials such as metals, plastics or glass, in a preferred embodiment, first container 12 and second container 16 are constructed of clear acrylic plastic, so as to be light in weight, inexpensive and permit viewing of the level of liquid 14 in respective containers. Bases 28 and 40, dividing member 64 between first container 12 and second container 16, venting mechanisms 18, 22, 30 and 34 may also be constructed of a clear acrylic plastic. In a preferred embodiment first container 12 and second container 16 each have a capacity of 1.25 liquid quarts. Also, in a preferred embodiment, liquid 14 comprises common drinking water.

The foregoing description and drawing merely explain and illustrate the invention and the invention is not limited thereto, except insofar as the appended claims are so limited as those skilled in the art who have the disclosure before them will be able to make modifications and variations therein without departing from the scope of the invention.

We claim:

1. An improved apparatus for the collection of atmospheric samples, comprising:
   a sealed first container member filled with liquid material therein;
   a sealed second container member positioned below said sealed first container member;
   first container venting means for the controlled introduction of the atmosphere surrounding said apparatus into said first container;
   second container venting means for the controlled dispersal of the atmosphere within said second container into the surrounding atmosphere;
   said first container venting means and said second container venting means comprising;
   a plurality of septum holding members attached to said first container member and said second container member respectively and extending therein, said septum holding members forming an airtight seal with said container members;
   said septum holding members each having a passageway therethrough into said container members;
   a septum positioned within said passageway, said septum forming an airtight seal within said passageway; and
   a hollow needle member having an aperture proximate its tip, said needle member being insertable through said septum whereby a gaseous atmosphere may pass into or out of the container member;
   restrictive flow channel means between said first and second container members for the controlled passage of said liquid therethrough, said passage of liquid creating a vacuum in said first container member whereby a portion of said surrounding atmosphere is controlledly drawn through said first container venting means and into said first container member where it is retained;
   sample removal means for permitting the withdrawal of a desired quantity of said retained atmosphere from within said first container member; and
   base means for the support of said apparatus.

2. An improved apparatus for the collection of atmospheric samples, comprising:
   a sealed first container member;
   a sealed second container member, in a first operating mode being positioned below said first container member, and in a second operating mode being positioned above said first container member;
   a selected quantity of liquid material, in said first operating mode initially filling said first container member, and in said second operating mode initially filling said second container member;
   first container top venting means for the controlled introduction of the atmosphere surrounding said apparatus into said first container member in said first operating mode;
   first container central venting means for the controlled dispersal of the atmosphere in said first container member into the atmosphere surrounding said apparatus in said second operating mode;
   second container top venting means for the controlled introduction of the atmosphere surrounding said apparatus into said second container member in said second operating mode;
   second container central venting means for the controlled dispersal of the atmosphere in said second container member into the atmosphere outside of said apparatus in said first operating mode;
   said first container top venting means, said first container central venting means, said second container top venting means, and said second container central venting means each comprising;
   a septum holding member attached to a respective container member and extending therein, said septum holding member forming an airtight seal with the container member;
   said septum holding member having a passageway therethrough into the container member;
   a septum positioned within said passageway, said septum forming an airtight seal within said passageway; and
   a hollow needle member having an aperture proximate its tip, said needle member being insertable through said septum whereby a gaseous atmosphere may pass into or out of the container member as required;
   restrictive flow channel means between said first and second container members for the controlled passage of said liquid therethrough so as to create a vacuum, in said first operating mode in said first container member and in said second operating mode in said second container member, thereby controlledly drawing a continuous stream of said surrounding atmosphere through said first container top venting means and into said first container member in said first mode, and through said second container top venting means and into said second container member in said second mode;
   sample removal means for permitting the withdrawal of a desired quantity of said retained atmosphere from said apparatus; and
   upper and lower base means for the support of said apparatus.

3. The invention according to claim 1 or 2 further comprising:
   quick drain valve means positioned between said first container member and second container member for the rapid drainage of said liquid whereby said apparatus may be quickly and easily prepared for a new sampling cycle.

4. The invention according to claim 1 in which, either the first or second container member may be utilized to obtain atmospheric samples by means of:

in said first operating mode, a hollow needle member positioned through said first container top venting means and a hollow needle member positioned through said second container central venting means whereby the atmosphere surrounding said apparatus is permitted to be introduced into said first container member, and the atmosphere within said second container member is permitted to be dispensed therefrom, thereby permitting said liquid to pass from said first container member into said second container below it; and in said second operating mode, the inversion of said first and second container members and a hollow needle member positioned through said second container top venting means and a hollow needle member positioned through said first container central venting means whereby the atmosphere surrounding said apparatus is permitted to be introduced into said second container member and the atmosphere within said first container member is permitted to be dispersed therefrom, thereby permitting said liquid to pass from said second container member into said first container below it.

5. The invention according to claim 1 or 2 in which said restrictive flow channel means comprises:
a tubular member having an orifice therethrough, said orifice having a diameter of 0.0032 inches whereby the passage of liquid therethrough is restrictively permitted.

6. The invention according to claim 1 in which said sample removal comprises:
a hypodermic syringe for withdrawal of a desired quantity of the atmosphere to be sampled from said apparatus through insertion of said syringe through said septum and into the container to be sampled; and
a sealed vacuum tub member adapted for injection of said atmospheric sample by said hypodermic syringe and for the retention therein of said sample.

7. The invention according to claim 1 or 2 in which said apparatus provides Time Weighted Average Samples of said surrounding atmosphere for chemical analysis thereof.

8. The invention according to claim 1 further including:
a plurality of needle holding members affixed to said apparatus for the retention of said hollow needle members.

9. The invention according to claim 1 in which each of said hollow needle members is a Size 20 hypodermic needle.

10. The invention according to claim 1 or 2 in which first and second container members are constructed from clear acrylic plastic so as to be light in weight, inexpensive and permit viewing of the level of said liquid in the containers.

11. The invention according to claim 7 in which said apparatus controlledly draws a stream of said surrounding atmosphere into said apparatus for a period of 4 hours, thereby permitting withdrawal of an atmospheric sample having an average concentration of the chemicals present in said atmosphere over a 4 hour period.

12. The invention according to claim 1 or 2 or 11 in which said first and second container members each have a capacity of 1.25 quarts.

13. The invention according to claim 1 or 2 in which liquid comprises:
common drinking water.

14. A method for the collection of atmospheric samples utilizing a collection apparatus having a sealed first container member filled with a liquid material, a second container member below said first container, first container venting means for the controlled introduction of the atmosphere surrounding said apparatus into said first container, second container venting means for the controlled dispersal of the atmosphere within said second container member, said first container venting means and said second container venting means comprising; a plurality of septum holding members attached to said first container member and said second container member respectively and extending therein, said septum holding members forming an airtight seal with said container members; said septum holding members each having a passageway therethrough into said container members; a septum positioned within said passageway, said septum forming an airtight seal within said passageway; and a hollow needle member having an aperture proximate its tip, said needle member being insertable through said septum whereby a gaseous atmosphere may pass into or out of the container member, restrictive flow channel means between said first and second container members for the controlled passage of said liquid therethrough, and base means for the support of said apparatus, said method comprising:
inserting a hollow needle member into said first container venting means thereby venting the atmosphere surrounding said apparatus into said first container member;
draining said liquid from said first container into said second container through said restrictive flow channel means;
creating a vacuum in said first container member by means of said liquid draining therefrom;
displacing said atmosphere within said second container member by means of said liquid draining therein; and
inserting a hollow needle member into said second container member thereby venting said atmosphere from said second container member out of said second container venting means.

15. The invention according to claim 14 including the additional steps of:
injecting a hypodermic syringe into said first container member;
drawing a measured quantity of said atmosphere into said syringe; and
injecting said measured quantity of said atmosphere into a gas chromatograph for chemical analysis thereof.

* * * * *